United States Patent
Perry

(10) Patent No.: US 10,517,304 B2
(45) Date of Patent: Dec. 31, 2019

(54) RODENTICIDE

(71) Applicant: Stephen C. Perry, Norwood, MA (US)

(72) Inventor: Stephen C. Perry, Norwood, MA (US)

(*) Notice: Subject to any disclaimer, the term of this patent is extended or adjusted under 35 U.S.C. 154(b) by 74 days.

(21) Appl. No.: 15/480,060

(22) Filed: Apr. 5, 2017

(65) Prior Publication Data

US 2018/0289017 A1    Oct. 11, 2018

(51) Int. Cl.

| | | |
|---|---|---|
| A01N 65/08 | (2009.01) | |
| A01N 25/00 | (2006.01) | |
| A01N 31/06 | (2006.01) | |
| A01N 37/04 | (2006.01) | |
| A01N 37/44 | (2006.01) | |
| A01N 43/16 | (2006.01) | |
| A01N 59/00 | (2006.01) | |
| A01N 59/06 | (2006.01) | |
| A01N 59/14 | (2006.01) | |
| A01N 59/16 | (2006.01) | |

(52) U.S. Cl.
CPC ........... *A01N 65/08* (2013.01); *A01N 25/004* (2013.01); *A01N 31/06* (2013.01); *A01N 37/04* (2013.01); *A01N 37/44* (2013.01); *A01N 43/16* (2013.01); *A01N 59/00* (2013.01); *A01N 59/06* (2013.01); *A01N 59/14* (2013.01); *A01N 59/16* (2013.01)

(58) Field of Classification Search
CPC ...... A01N 25/004; A01N 25/00; A01N 59/00; A01N 59/06; A01N 59/04; A01N 59/14; A01N 59/16

See application file for complete search history.

(56) References Cited

U.S. PATENT DOCUMENTS

| | | | |
|---|---|---|---|
| 3,624,198 A | 11/1971 | Arbaugh | |
| 8,574,638 B1 | 11/2013 | Perry | |
| 2005/0181003 A1 | 8/2005 | Endepols et al. | |
| 2014/0271932 A1 | 9/2014 | Rubel et al. | |
| 2015/0147289 A1* | 5/2015 | Bajomi | A01N 41/04 424/84 |
| 2016/0050910 A1* | 2/2016 | Twydell | A01N 25/004 514/167 |
| 2017/0028449 A1* | 2/2017 | Fernholz | B08B 9/08 |

FOREIGN PATENT DOCUMENTS

| | | |
|---|---|---|
| EP | 2 742 801 | 6/2014 |
| EP | 3 295 793 | 3/2018 |
| WO | 2004/062362 | 7/2004 |
| WO | 2013/134267 A1 | 9/2013 |
| WO | 2014/154621 | 10/2014 |
| WO | 2016/201178 A1 | 12/2016 |

OTHER PUBLICATIONS

Carbonates (Chemistry LibreTexts pp. 1-2, https://chem.libretexts.org/Bookshelves/Inorganic_Chemistry/Supplemental_Modules_(Inorganic_Chemistry)/Descriptive_Chemistry/Main_Group_Reactions/Compounds/Carbonates accessed Apr. 11, 2019, last updated Jan. 20, 2015).*

Mandl (Propylene Glycol in Food: Is This Additive Safe? accessed Mar. 2, 2018 accessed via https://www.healthline.com/nutrition/propylene-glycol on Apr. 11, 2019, p. 1-18).*

International Search Report for PCT/US2018/25656, dated May 24, 2018, 2 pages.

Written Opinion for PCT/US2018/25656, dated May 24, 2018, 8 pages.

Anonmyous: "Rodenticide," Wikipedia, Mar. 14, 2017, Retrieved from the internet: URL:http://web.archive.org/web/20170314124650/https://en.wikipedia.org/wiki/Rodenticide.

European Search Report dated Aug. 21, 2018, Application Serial No. EP 18165952, in the name of Stephen C. Perry.

* cited by examiner

*Primary Examiner* — Kortney L. Klinkel

(74) *Attorney, Agent, or Firm* — Johnson & Martin, P.A.; James David Johnson

(57) ABSTRACT

A rodenticide composition is described along with a method for using the same to exterminate rodents. The composition features a mixture of a dehydrant, a composition for producing endogenous gas, a dietary emulsifier, a hypercalcemia promoter, and a source of cellulose. After consumption of the composition by a rodent, the dehydrant and source of cellulose cause the rodent to experience dehydration, while the endogenous gas produced by the composition causes bloating and increased digestive stress. The dietary emulsifier and hypercalcemia promoter cause digestive stress, which reduces the rodent's desire to feed and quickens dehydration and death. Once the rodenticide composition is prepared, it may be placed in areas frequented by or infested with rodents so as to kill the rodents once they consume the composition. One or more flavorings, coloring agents, and weather resistant materials may also be added to the composition.

27 Claims, No Drawings

RODENTICIDE

FIELD OF THE INVENTION

The invention relates to a pesticide. More particularly, the invention relates to a rodenticide useful for exterminating rodents but that is non-toxic to humans and other animals.

BACKGROUND

Pesticides, and particularly rodenticides, can be harmful to humans and other animals that unknowingly consume them or otherwise come into contact with them. In the past, rodenticides ingested intentionally and unintentionally by humans resulted in illness and death. Presently, conventional rodenticides ingested by animals other than the pests (namely, mice and rats) for which they are intended also result in the unintentional killing of those animals. Pet animals and wildlife are both harmed or killed by conventional rodenticide usage.

Vomiting (also called emesis) is a reflexive act caused by coordinated contractions of various muscles that eject stomach contents forcefully through an animal's mouth. Humans and many other animals are capable of vomiting as a natural reaction to purge toxic substances from the body. During vomiting, the muscles of the abdomen and chest contract and the diaphragm spasms downward and inward exerting pressure on the stomach. Next, and nearly simultaneously, the cardiac sphincter, which is a part of the diaphragm surrounding the esophagus, relaxes to assist in opening the esophagus. The longitudinal muscle of the esophagus contracts, which further opens the cardiac sphincter, and the resulting pressure forces contents of the stomach up into the esophagus and out of the animal's mouth.

Rats and many other rodents are unable to vomit, i.e., cannot produce an emetic reflex. Physiologically, rats have a powerful barrier between the stomach and the esophagus but lack sufficient esophageal muscle strength to overcome and open this barrier by force, which is necessary for vomiting. In humans and other animals, the emetic reflex requires that two muscles of the diaphragm contract independently, but rats are unable to dissociate the activity of these two muscles so that they may produce the independent contractions necessary for vomiting. In addition, rats lack complex neural connections that are present within the brain stem and between the brain stem and viscera of humans and other animals that coordinate the numerous muscles that produce the emetic reflex.

While rats are unable to vomit, they do exhibit other behavior-based techniques to avoid consumption of and poisoning by toxic substances. For example, rats learn to avoid certain foods that make them sick. When a rat discovers a new food, the rat consumes a small amount of the food, and if the rat becomes ill after ingesting the food, the rat learns to scrupulously avoid that food in the future. Rats learn to identify the food that is to be avoided by its taste and smell. Rats experiencing nausea also display pica, which is the consumption of clay or other non-food materials. By ingesting clay, some toxins are bound in the rat's stomach, which assists in reducing the effects of the toxin as experienced by the rat.

While rats are unable to vomit, they can regurgitate. Regurgitation is not the same as emesis and does not produce the forceful expulsion of the stomach contents through the esophagus and out of the mouth. In studies, when a rat is fed a diet of bulky food items, when the rat regurgitates stomach contents, the regurgitant is pasty and thick in composition and, as a result of the rat's tongue action, becomes packed as a plug within the rat's pharynx, larynx and esophagus. Because the regurgitant forms a plug, the rat chokes and often dies.

The rat's esophagus includes inner circular and outer longitudinal layers of striated muscle. These two layers of striated muscle become smooth muscle near the esophagus's point of attachment with the rat's stomach. A gastroesophageal barrier separates and closes off the rat's esophagus from its stomach. The gastroesophageal barrier is formed by a crural sling, a lower esophageal sphincter, and intraabdominal esophagus that lie between the crural sling and lower esophageal sphincter. The crural sling is part of the rat's diaphragm and is composed of a U-shaped bundle of fibers that wraps around the esophagus and attaches to the rat's vertebrae so that when the crural sling contracts, the rat's esophagus is pinched closed. The rat's diaphragm is formed by two muscles: the crural sling and the costal muscle, which is attached to the rat's rib cage. The lower esophageal sphincter is a circular muscle that surrounds the base of the esophagus and, at its lower edge, includes muscle fibers that insert into the limiting ridge, as described below.

The stomach of a rat includes two parts, i.e., a forestomach and a corpus. The forestomach is a non-glandular, thin-walled portion that receives the esophagus and serves as an initial holding chamber for food that is consumed. In rats, the forestomach's walls are similar to walls of the rat's esophagus. Unlike the forestomach, the corpus is a glandular, thick-walled section having walls that include secretory glands, which produce mucus and digestive enzymes. In rats, digestion begins in the stomach's corpus. A pyloric sphincter controls movement of stomach contents from the corpus into the intestines. The forestomach and corpus are separated by a limiting ridge (also called the margo plicatus), a low fold of tissue that extends circumferentially from the large curvature of the stomach to the small curvature of the stomach just below the esophagus. At the esophagus, the limiting ridge forms a U-shape that nearly surrounds the esophageal opening into the forestomach and the muscle fibers of the lower esophageal sphincter are inserted into the limiting ridge. Due to this anatomical structure, when a rat's lower esophageal sphincter contracts, both the walls of the rat's esophagus and the sides of the limiting ridge's U-shaped portion are pulled together, which tightly closes the esophageal opening in the rat's stomach thereby preventing stomach contents from being expelled by vomiting.

Pressure at the two ends of a rat's gastroesophageal barrier is much higher than the pressure found in the rat's thorax or abdomen during any phase of the breathing cycle. The strength and pressure of this barrier make reflux in rats nearly impossible although rats may engage in regurgitation. Rats are not capable of vomiting because, for several reasons explained below, they cannot produce the necessary coordinated muscular contractions to overcome this powerful barrier.

Rats are incapable of relaxing the crural sling while simultaneously contracting the remainder of the diaphragm. The rat's esophagus passes through the crural sling, and as explained above, when the crural sling of the diaphragm contracts, the rat's esophagus is pinched tightly closed. Rats are physiologically incapable of dissociating the activity of the crural sling and costal muscle of their diaphragm, and as a result, a rat cannot relax the crural sling while simultaneously contracting the costal muscle. Instead, in rats as opposed to in humans, both diaphragm muscles always contract or relax together. Rats' inability to separately and selectively control its two diaphragmatic muscles render their bodies incapable of producing the pressure on the stomach necessary to open the crural sling so as to allow their stomach contents to be expelled.

Rats are also unable to open their esophageal sphincter to permit the forceful expulsion of stomach contents during vomiting. In rats, the esophagus consists of a thin, weak unstriated, longitudinal muscle at its point of connection with the stomach, which is not sufficiently strong to open the rat's lower esophageal sphincter so as to allow expulsion of the rat's stomach contents.

Unlike emetic animals (including humans), rats and other nonemetics lack neural connections within the brain and between the brainstem and viscera that are necessary to coordinate the numerous muscles that produce the emetic reflex. While the brainstem nuclei and the muscle systems used in vomiting are present in rats and other nonemetics, the complex neural connections between the nuclei or between the brainstem and viscera, which are necessary to produce coordinated muscular contractions required for vomiting, are absent.

A need exists for a rodenticide that is safe and non-toxic if consumed by humans or non-rodent pets and wildlife.

SUMMARY

The invention relates to a rodenticide composition and method for using the same to exterminate rodents. The rodenticide composition features a mixture that includes a dehydrant, a composition for producing endogenous gas, a dietary emulsifier, a hypercalcemia promoter, and a source of cellulose. Examples of these ingredients and of other ingredients that may be included in the rodenticide composition are identified in U.S. Pat. No. 8,574,638, which is incorporated in its entirety herein by this reference. After consumption of the composition by a rodent, the dehydrant and source of cellulose cause the rodent to experience dehydration. The endogenous gas produced by the composition causes bloating and increased digestive stress. The dietary emulsifier and hypercalcemia promoter also cause digestive stress, which reduces the rodent's desire to feed and quickens dehydration and death. Once the rodenticide composition is prepared, it may be placed in areas frequented by or infested with rodents so as to kill the rodents once they consume the composition. Flavoring to entice consumption and weather resistant material to prolong effectiveness when exposed to water and the elements may also be added to the composition. One or more coloring agents optionally may also be added to the composition as ingredients. Once the rodenticide composition is prepared, it may be placed in areas frequented by or infested with rodents so as to kill the rodents once they consume the composition. The rodenticide is effective for exterminating various species of rodents including rats, mice, voles, chipmunks, ground squirrels, groundhogs, nutrias, beavers, and other rodent pests.

Because rats do not have an emetic reflex as do humans and some other animals, rats cannot experience emesis (i.e., vomiting) to expel the contents of the stomach through the mouth. This physiological feature of rats and some other rodents provides a means for creating non-toxic rodenticides that are safe if consumed by humans, pets, or other non-rodent wildlife while being lethal to rats. The rodenticide composition can be consumed as a food source by rats. After ingestion of the rodenticide composition, dehydration of the rat commences, which causes the rat's blood to thicken as well as circulatory collapse. A rat that has consumed the rodenticide composition will become lethargic and retreat to its burrow where it lapses into a coma and dies. Rodent activity declines as death occurs within 4 to 7 days after regular ingestion of the rodenticide composition.

The rodenticide composition provides an advantage in that it is non-toxic to humans and other non-rodent animals. The rodenticide composition is also advantageous because it can be prepared efficiently and inexpensively from readily available, plentiful, inexpensive ingredients. The rodenticide composition also provides an advantage in that rodents that consume it do not immediately experience symptoms of poisoning, and thus, are undeterred in consuming it as they often are by learning after consuming small portions of other rodenticides. The rodenticide composition provides still another advantage in that a rodent's consumption of soil will not work to counteract the lethal effects of the composition because it is not a traditional rodenticide that contains toxins.

Accordingly, the invention features a rodenticide that includes a mixture of a dehydrant, a composition for producing endogenous gas, a dietary emulsifier, a hypercalcemia promoter, and a source of cellulose.

In another aspect, the invention can feature the dehydrant including or being a grain-based cellulosic composition, a nut-based cellulosic composition, a legume-based cellulosic composition, a starchy tuber-based cellulosic composition, cellulose fibers, activated alumina, aerogel, benzophenone, bentonite clay, calcium chloride, calcium sulfate, caramel, cellulose fibers, cobalt (II) chloride, copper (II) sulfate, ethanol, glycerol, honey, lithium bromide, lithium chloride, magnesium perchlorate, magnesium sulfate, methanol, perlite, potassium carbonate, potassium hydroxide, silica, silica gel, fumed silica, sodium, sodium chlorate, sodium chloride, sodium hydroxide, sucrose, sulfuric acid, vermiculite, zinc chloride, any other suitable dehydrant, a combination of two or more of the foregoing, or any other suitable material derived from any of the foregoing.

In another aspect, the invention can feature the endogenous gas including or being oxygen and wherein the composition for producing endogenous gas includes an alkali carbonate, a peroxide, yeast, a combination of two or more of the foregoing, any other suitable composition for producing endogenous gas, or any other suitable material derived from any of the foregoing.

In another aspect, the invention can feature the composition for producing endogenous gas including or being sodium percarbonate, magnesium percarbonate, zinc percarbonate, calcium peroxide, calcium percarbonate, magnesium peroxide, zinc peroxide, sodium perborate, potassium monopersulfate, tetraacetylethylenediamine, any other suitable composition for producing endogenous gas, yeast, a combination of two or more of the foregoing, or any other suitable material derived from any of the foregoing.

In another aspect, the invention can feature the dietary emulsifier including or being carboxymethyl cellulose, polyoxyethylene (20) sorbitan monooleate, both, any other suitable dietary emulsifier, or any other suitable material derived from any of the foregoing.

In another aspect, the invention can feature the hypercalcemia promoter including or being calcium carbonate, calcium glycerate, calcium citrate, calcium lactate, calcium gluconate, a calcium uptake enhancer, bone meal, any other suitable hypercalcemia promoter, a combination of two or more of the foregoing, or any other suitable material derived from any of the foregoing.

In another aspect, the invention can feature the calcium uptake enhancer including or being cholecalciferol, ergocalciferol, L-lysine, L-Valine, L-tryptophan, any other suitable calcium uptake enhancer, a combination of two or more of the foregoing, or any other suitable material derived from any of the foregoing.

In another aspect, the invention can feature the source of cellulose including or being carboxymethyl cellulose, cardboard, cellulose acetate, regenerated cellulose, hydroxyethyl cellulose, hydroxypropyl cellulose, hydroxypropylmethyl cellulose, methylcellulose, pectin, sodium carboxymethyl cellulose, cornmeal, corn grits, corn cobs, corn gluten meal, any other suitable source of cellulose, a combination of two or more of the foregoing, or any other suitable material derived from any of the foregoing.

In another aspect, the invention can feature the composition further including an irritant, wherein the irritant is or includes fish oil, caffeine, coffee grounds, sodium nitrite, citric acid, soybean oil, a magnesium-containing compound, vinegar, ammonium benzoate, any other suitable irritant, a combination of two or more of the foregoing, or any other suitable material derived from any of the foregoing.

In another aspect, the invention can feature the magnesium-containing compound including or being magnesium sulfate, magnesium chloride, magnesium carbonate, magnesium bicarbonate, magnesium phosphate, magnesium hydroxide, magnesium oxide, any other suitable magnesium-containing compound, a combination of two or more of the foregoing, or any other suitable material derived from any of the foregoing.

In another aspect, the invention can feature the mixture further including a non-water soluble material that inhibits deterioration in wet and damp environments.

In another aspect, the invention can feature the non-water soluble material including or being beeswax, paraffin wax, soybean oil, an ester of ammonia, an ester of butyl, an ester of calcium, an ester of glyceryl, fish oil, ammonium stearate, animal glue, any other suitable non-water soluble material, a combination of two or more of the foregoing, or any other suitable material derived from any of the foregoing.

In another aspect, the invention can feature a flavoring, wherein the flavoring is or includes cocoa, peanut butter, cheese, egg yolk, sulfur, fish oil, fish meal, dimethyl disulfide, syrup, peanuts, sorbitol, sucralose, sucrose, fructose, molasses, cat food, malt flavor, nutria meat, dried blood, any other suitable flavoring, a combination of two or more of the foregoing, or any other suitable material derived from any of the foregoing.

In another aspect, the invention can feature a coloring agent, wherein the coloring agent is or includes FD&C Red No. 3, FD&C Red No. 40, red cabbage color, FD&C Yellow No. 5, FD&C Yellow No. 6, FD&C Blue No. 1, C.I. Pigment Blue No. 29, FD&C Blue No. 2, FD&C Green No. 3, any other suitable coloring agent, a combination of two or more of the foregoing, or any other suitable material derived from any of the foregoing.

The invention also features a rodenticide that includes a mixture of: a dehydrant including cellulose fibers, silica gel, perlite, sodium chloride, any other suitable dehydrant, or a combination of two or more of the foregoing; a composition for producing endogenous gas, wherein the gas includes oxygen and the composition for producing endogenous gas includes calcium percarbonate, calcium peroxide, or both; a dietary emulsifier including carboxymethylcellulose, polyoxyethylene (20) sorbitan monooleate, or both; a hypercalcemia promoter including a mixture of calcium carbonate and cholecalciferol; an irritant; and a source of cellulose.

In another aspect, the invention can feature the dehydrant including or being cellulose fibers, silica gel, or both.

In another aspect, the invention can feature the composition for producing endogenous gas including or being calcium percarbonate.

In another aspect, the invention can feature the dietary emulsifier including or being polyoxyethylene (20) sorbitan monooleate.

In another aspect, the invention can feature the hypercalcemia promoter including or being a mixture of calcium carbonate, cholecalciferol, and L-lysine.

In another aspect, the invention can feature the source of cellulose including or being corn cobs, carboxymethyl cellulose, or both.

In another aspect, the invention can feature an irritant, wherein the irritant is or includes citric acid, coffee grounds, or both.

In another aspect, the invention can feature the mixture further including a non-water soluble material that inhibits deterioration in wet and damp environments.

In another aspect, the invention can feature a coloring agent, wherein the coloring agent is or includes a red coloring agent or a yellow coloring agent.

The invention also features a rodenticide that includes a mixture of: a dehydrant including cellulose fibers, silica gel, or both; a composition for producing endogenous gas, wherein the gas includes oxygen and the composition for producing endogenous gas comprises calcium percarbonate; a dietary emulsifier including polyoxyethylene (20) sorbitan monooleate; a hypercalcemia promoter including a mixture of calcium carbonate, cholecalciferol, and L-lysine; an irritant including fish oil, caffeine, coffee grounds, sodium nitrite, citric acid, soybean oil, a magnesium-containing compound, any other suitable irritant, a combination of two or more of the foregoing, or any other suitable material derived from any of the foregoing; and a source of cellulose.

In another aspect, the invention can feature the irritant including or being citric acid, coffee grounds, or both.

In another aspect, the invention can feature the source of cellulose including or being corn cobs, carboxymethyl cellulose, or both.

In another aspect, the invention can feature the mixture further including a non-water soluble material that inhibits deterioration in wet and damp environments.

In another aspect, the invention can feature a coloring agent, wherein the coloring agent is or includes a red coloring agent or a yellow coloring agent A method of the invention can be used to exterminate rodents, and the method can include the steps of: (a) preparing a rodenticide composition that includes a mixture of a dehydrant, a composition for producing endogenous gas, a dietary emulsifier, a hypercalcemia promoter, and a source of cellulose; and (b) placing an amount of the rodenticide composition sufficient to kill a rodent in an area in which the extermination of rodents is desired, wherein the rodent is killed after consuming the rodenticide composition.

Another method of the invention can feature the rodenticide composition further including at least one additional ingredient selected from among: an irritant, a non-water soluble material that inhibits deterioration in wet and damp environments, and a coloring agent.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control.

DETAILED DESCRIPTION

The present invention is best understood by reference to the description set forth herein. Those skilled in the art will readily appreciate that the detailed description given herein is for explanatory purposes as the invention extends beyond these limited embodiments. For example, in light of the teachings of the present invention, those skilled in the art will recognize a multiplicity of alternate and suitable approaches, depending upon the needs of the particular application, to implement the functionality of any given detail described herein beyond the particular implementation choices in the following embodiments described and shown. That is, numerous modifications and variations of the invention exist that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The present invention is not limited to the particular methodology, compounds, materials, manufacturing techniques, uses, and applications, described herein, as these may vary. The terminology used herein is used for the purpose of describing particular embodiments only, and is not intended to limit the scope of the present invention. As used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means.

All conjunctions used herein are to be understood in the most inclusive sense possible. Thus, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise. Structures described herein are to be understood also to refer to functional equivalents of such structures. Language that may be construed to express approximation should be so understood unless the context clearly dictates otherwise.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "having" should be interpreted as "having at least"; the term "includes" should be interpreted as "includes but is not limited to"; the term "example" is used to provide exemplary instances of the item in discussion, not an exhaustive or limiting list thereof; and use of terms like "preferably," "preferred," "desired," "desirable," or "exemplary" and words of similar meaning should not be understood as implying that certain features are critical, essential, or even important to the structure or function of the invention, but instead as merely intended to highlight alternative or additional features that may or may not be utilized in a particular embodiment of the invention.

Those skilled in the art will also understand that if a specific number of an introduced claim recitation is intended, such an intent will be explicitly recited in the claim, and in the absence of such recitation no such intent is present. For example, as an aid to understanding, the appended claims may contain usage of the introductory phrases "at least one" and "one or more" to introduce claim recitations; however, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C" is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C" is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

All numbers expressing dimensions, quantities of ingredients, reaction conditions, and so forth used in the specification are to be understood as being modified in all instances by the term "about" unless expressly stated otherwise. Accordingly, unless indicated to the contrary, the numerical parameters set forth herein are approximations that may vary depending upon the desired properties sought to be obtained.

The invention provides a rodenticide composition and method for using the same to exterminate rodents. The rodenticide composition includes a mixture of: a dehydrant, a composition for producing endogenous gas, a dietary emulsifier, and a source of cellulose. In the most exemplary embodiments, the rodenticide composition will also include a hypercalcemia promoter. In other exemplary embodiments, the rodenticide composition can include one or more irritants as ingredients. In some embodiments, the rodenticide composition can also include a flavoring, a weathering agent, or both.

The dehydrant of the rodenticide is a composition or ingredient that causes a rodent to experience dehydration after it is consumed. Hygroscopic desiccant materials are useful as dehydrants in the rodenticide due to their ability to absorb water from their surroundings (in this case, water in the rodent's digestive system). Such hygroscopic materials can also include deliquescents that readily dissolve in water until fully dissolved. Examples of deliquescents include sodium chloride, zinc chloride, calcium chloride, potassium hydroxide, and sodium hydroxide. The dehydrant is selected from among: a grain-based cellulosic composition, a nut-based cellulosic composition, a legume-based cellulosic composition, a starchy tuber-based cellulosic composition, alpha cellulose, cellulose fibers, activated alumina, aerogel, benzophenone, bentonite clay, calcium chloride, calcium sulfate, caramel, cellulose fibers, cobalt (II) chloride, copper (II) sulfate, ethanol, glycerol, honey, lithium bromide, lithium chloride, magnesium perchlorate, magnesium sulfate, methanol, perlite, potassium carbonate, potassium hydroxide, silica, silica gel, fumed silica, sodium, sodium chlorate, sodium chloride, sodium hydroxide, sucrose, sulfuric acid, vermiculite, zinc chloride, any other suitable dehydrant, a combination of two or more of the foregoing, or any other suitable material derived from any of the foregoing. In certain exemplary embodiments, the dehydrant can be one or more naturally occurring compositions or ingredients. In other embodiments, the dehydrant can be one or more artificial or manmade compositions or ingredients. In still other embodiments, the dehydrant can be a mixture of one or more naturally occurring compositions or ingredients and one or more artificial or manmade compositions or ingredients.

In preferred embodiments of the rodenticide composition, the dehydrant is selected from among cellulose fibers, silica gel, perlite, sodium chloride, or a combination of two or more of the foregoing. In the most preferred embodiments of the rodenticide composition, the dehydrant is selected from among cellulose fibers, silica gel, or both.

The dehydrant may be included in the rodenticide composition in a percentage by weight of about 20% to about 60%. For example, the dehydrant may be incorporated into the rodenticide composition in about 15, 16, 17, 17.5, 18, 18.5, 18.75, 18.9, 18.99, 19, 19.01, 19.05, 19.1, 19.2, 19.25, 19.3, 19.4, 19.41, 19.45, 19.49, 19.5, 19.51, 19.55, 19.59, 19.6, 19.7, 19.75, 19.8, 19.9, 19.91, 19.95, 19.99, 20, 20.01, 20.1, 20.2, 20.25, 20.3, 20.4, 20.5, 20.6, 20.7, 20.75, 20.8, 20.9, 20.95, 20.99, 21, 22, 23, 24, 25, 26, 27, 27.5, 28, 29, 30, 35, 40, 41, 41.5, 41.9, 42, 42.1, 42.2, 42.25, 42.3, 42.4, 42.5, 42.6, 42.7, 42.75, 42.8, 42.9, 42.95, 42.99, 43, 43.01, 43.05, 43.09, 43.1, 43.2, 43.25, 43.3, 43.4, 43.5, 43.6, 43.7, 43.75, 43.8, 43.9, 43.91, 43.95, 43.99, 44, 44.1, 44.5, 45, 46, 47, 48, 49, 50, 51, 52, 53, 54, 55, 56, 57, 58, 59, 59.1, 59.2, 59.25, 59.3, 59.4, 59.5, 59.6, 59.7, 59.75, 59.8, 59.9, 59.91, 59.95, 59.99, 60, 60.01, 60.05, 60.09, 60.1, 60.2, 60.25, 60.3, 60.4, 60.41, 60.45, 60.5, 60.51, 60.55, 60.59, 60.6, 60.7, 60.75, 60.8, 60.9, 60.91, 60.95, 60.99, 61, 61.01, 61.1, 61.25, 61.5, 62, 63, 64, 65, 70, 75, 80, 85, 86, 90, or 95 percent by weight. The rodenticide composition can include the dehydrant in a percentage by weight of about a lower limit to about an upper limit, wherein the lower limit is a percentage by weight selected from the foregoing percentages by weight and the upper limit is a percentage by weight selected from the foregoing percentages by weight that is higher than the lower limit. In a preferred range, the rodenticide composition can include the dehydrant in a percentage by weight of about 20% to about 60%. In a most preferred range, the rodenticide composition can include the dehydrant in a percentage by weight of about 30% to about 50%.

In an exemplary embodiment, the dehydrant can be included in the composition at about 43% of the composition by weight.

The composition for producing endogenous gas of the rodenticide composition is an alkali carbonate, a peroxide, yeast, a combination of two or more of the foregoing, or any other suitable material derived from any of the foregoing. Once ingested by a rodent, the composition for producing endogenous gas produces oxygen as the endogenous gas. The endogenous gas causes bloating, discomfort, and digestive stress that decreases the rodent's desire to eat, which further dehydrates the rodent and hastens death. The rodenticide's composition for producing endogenous gas is a composition selected from among: sodium percarbonate, magnesium percarbonate, zinc percarbonate, calcium peroxide, calcium percarbonate, magnesium peroxide, zinc peroxide, sodium perborate, potassium monopersulfate, tetraacetylethylenediamine, yeast, any other suitable composition or ingredient for producing endogenous gas, a combination of two or more of the foregoing, or any other suitable material derived from any of the foregoing. In certain exemplary embodiments, the composition for producing endogenous gas can be one or more naturally occurring compositions or ingredients. In other embodiments, the composition for producing endogenous gas can be one or more artificial or manmade compositions or ingredients. In still other embodiments, the composition for producing endogenous gas can be a mixture of one or more naturally occurring compositions or ingredients and one or more artificial or manmade compositions or ingredients.

In preferred embodiments of the rodenticide composition, the composition for producing endogenous gas is selected from among calcium percarbonate, calcium peroxide or both. In the most preferred embodiments of the rodenticide composition, the composition for producing endogenous gas is calcium percarbonate.

The composition for producing endogenous gas may be included in the rodenticide composition in a percentage by weight of about 2% to about 10%. For example, the composition for producing endogenous gas may be incorporated into the rodenticide composition in about 0.1, 0.101, 0.105, 0.11, 0.12, 0.13, 0.14, 0.15, 0.16, 0.17, 0.18, 0.19, 0.195, 0.199, 0.2, 0.201, 0.205, 0.21, 0.22, 0.225, 0.23, 0.24, 0.241, 0.245, 0.249, 0.25, 0.251, 0.255, 0.26, 0.27, 0.275, 0.28, 0.29, 0.291, 0.295, 0.299, 0.3, 0.31, 0.32, 0.325, 0.33, 0.34, 0.35, 0.36, 0.37, 0.375, 0.38, 0.39, 0.4, 0.41, 0.45, 0.49, 0.5, 0.51, 0.55, 0.59, 0.6, 0.7, 0.75, 0.8, 0.9, 0.91, 0.95, 0.99, 1, 1.01, 1.1, 1.2, 1.25, 1.3, 1.4, 1.5, 1.6, 1.7, 1.75, 1.8, 1.9, 1.95, 1.99, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 3.95, 3.99, 4, 4.01, 4.05, 4.09, 4.1, 4.15, 4.19, 4.2, 42.25, 4.3, 4.4, 4.5, 4.6, 4.7, 4.75, 4.8, 4.9, 4.95, 4.99, 5, 5.01, 5.05, 5.09, 5.1, 5.2, 5.25, 5.3, 5.4, 5.5, 5.6, 5.7, 5.75, 5.8, 5.9, 5.91, 5.95, 5.99, 6, 6.1, 6.5, 7, 7.5, 7.9, 7.95, 7.99, 8, 8.1, 8.2, 8.25, 8.3, 8.4, 8.5, 8.6, 8.7, 8.75, 8.8, 8.9, 9, 9.1, 9.2, 9.25, 9.3, 9.4, 9.5, 9.6, 9.7, 9.75, 9.8, 9.9, 9.91, 9.95, 9.99, 10, 10.1, 10.2, 10.25, 10.3, 10.4, 10.5, 10.6, 10.7, 10.75, 10.8, 10.9, 11, 12, 13, 14, 15, or 20 percent by weight. The rodenticide composition can include the composition for producing endogenous gas in a percentage by weight of about a lower limit to about an upper limit, wherein the lower limit is a percentage by weight selected from the foregoing percentages by weight and the upper limit is a percentage by weight selected from the foregoing percentages by weight that is higher than the lower limit. In a preferred range, the rodenticide composition can include the composition for producing endogenous gas in a percentage by weight of about 2% to about 10%. In a most preferred range, the rodenticide composition can include the composition for producing endogenous gas in a percentage by weight of about 4% to about 8%. In an exemplary embodiment, the composition for producing endogenous gas can be included in the composition at about 6% of the composition by weight.

The dietary emulsifier is a composition that disrupts the gut microbiota in rodents and promotes colitis and metabolic syndrome. The initial dietary stress caused in the rodent after consumption of the dietary emulsifier contained in the rodenticide reduces the rodent's desire to feed and increases dehydration and hastens death. The rodent's intestine is protected from its microbiota via multi-layered mucus structures that cover the intestinal surface, thereby allowing the vast majority of gut bacteria to be kept at a safe distance from epithelial cells that line the intestine. Agents that disrupt mucus-bacterial interactions can promote diseases associated with gut inflammation. Common food-grade emulsifiers can readily disrupt mucus-bacterial interactions in rodents leading to gut inflammation. Low concentrations of one or both of these two commonly used food grade emulsifiers, carboxymethylcellulose and polyoxyethylene (20) sorbitan monooleate, induce low-grade inflammation and metabolic syndrome in wild-type rodent hosts and promoted robust colitis in mice predisposed to this disorder. Further, polyoxyethylene (20) sorbitan monooleate produces mild to moderate depression of a rodent's central nervous system with a marked reduction in locomotor activity and causes both ataxia and paralytic response.

The dietary emulsifier of the rodenticide composition is carboxymethylcellulose, polyoxyethylene (20) sorbitan monooleate, both, any other suitable dietary emulsifier, or any other suitable material derived from any of the foregoing. In the most preferred embodiments of the rodenticide composition, the composition for producing endogenous gas is polyoxyethylene (20) sorbitan monooleate.

The dietary emulsifier may be included in the rodenticide composition in a percentage by weight of about 0.25% to about 5%. For example, the dietary emulsifier may be incorporated into the rodenticide composition in about 0.001, 0.005, 0.009, 0.01, 0.015, 0.019, 0.02, 0.025, 0.03, 0.04, 0.05, 0.06, 0.07, 0.08, 0.09, 0.095, 0.099, 0.1, 0.101, 0.105, 0.11, 0.12, 0.13, 0.14, 0.15, 0.16, 0.17, 0.18, 0.19, 0.195, 0.199, 0.2, 0.201, 0.205, 0.21, 0.22, 0.225, 0.23, 0.24, 0.241, 0.245, 0.249, 0.25, 0.251, 0.255, 0.26, 0.27, 0.275, 0.28, 0.29, 0.291, 0.295, 0.299, 0.3, 0.31, 0.32, 0.325, 0.33, 0.34, 0.35, 0.36, 0.37, 0.375, 0.38, 0.39, 0.4, 0.41, 0.45, 0.49, 0.5, 0.51, 0.55, 0.59, 0.6, 0.7, 0.75, 0.8, 0.9, 0.91, 0.95, 0.99, 1, 1.01, 1.1, 1.2, 1.25, 1.3, 1.4, 1.5, 1.6, 1.7, 1.75, 1.8, 1.9, 1.95, 1.99, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 3.95, 3.99, 4, 4.01, 4.05, 4.09, 4.1, 4.15, 4.19, 4.2, 42.25, 4.3, 4.4, 4.5, 4.6, 4.7, 4.75, 4.8, 4.9, 4.95, 4.99, 5, 5.01, 5.05, 5.09, 5.1, 5.2, 5.25, 5.3, 5.4, 5.5, 5.6, 5.7, 5.75, 5.8, 5.9, 5.91, 5.95, 5.99, 6, 6.1, 6.5, 7, 8, 9, or 10 percent by weight. The rodenticide composition can include the dietary emulsifier in a percentage by weight of about a lower limit to about an upper limit, wherein the lower limit is a percentage by weight selected from the foregoing percentages by weight and the upper limit is a percentage by weight selected from the foregoing percentages by weight that is higher than the lower limit. In a preferred range, the rodenticide composition can include the dietary emulsifier in a percentage by weight of about 0.25% to about 5%. In a most preferred range, the rodenticide composition can include the dietary emulsifier in a percentage by weight of about 0.5% to about 3%. In an exemplary embodiment, the dietary emulsifier can be included in the composition at about 1% of the composition by weight.

The hypercalcemia promoter of the rodenticide composition causes long-term hypercalcemia by increasing calcium levels in the blood. Hypercalcemia further causes elevated arterial blood pressure and increased cardiac muscle contraction, which leads to polyuria and dehydration that eventually cause death. The hypercalcemia promoter also causes digestive stress and metabolic disorder in the short term, which reduces the rodent's desire to eat, thereby increasing dehydration and hastening death of the rodent.

The hypercalcemia promoter of the rodenticide composition is selected from among: calcium carbonate, calcium glycerate, calcium citrate, calcium lactate, calcium gluconate, a calcium uptake enhancer, bone meal, any other suitable source of a hypercalcemia promoter, a combination of two or more of the foregoing, or any other suitable material derived from any of the foregoing. The calcium uptake enhancer can be selected from among: cholecalciferol, ergocalciferol, L-lysine, L-Valine, L-tryptophan, any other suitable calcium uptake enhancer, a combination of two or more of the foregoing, or any other suitable material derived from any of the foregoing. Some embodiments of the rodenticide composition may not include a hypercalcemia promoter.

In preferred embodiments of the rodenticide composition, the hypercalcemia promoter is a combination of calcium carbonate and cholecalciferol. In the most preferred embodiments of the rodenticide composition, the hypercalcemia promoter is a combination of calcium carbonate, cholecalciferol, and L-lysine.

The hypercalcemia promoter may be included in the rodenticide composition in a percentage by weight of about 0.05% to about 4%. For example, the hypercalcemia promoter may be incorporated into the rodenticide composition in about 0.001, 0.005, 0.009, 0.01, 0.015, 0.019, 0.02, 0.025, 0.03, 0.035, 0.039, 0.04, 0.041, 0.042, 0.0425, 0.043, 0.044, 0.045, 0.046, 0.047, 0.0475, 0.048, 0.049, 0.0491, 0.0495, 0.0499, 0.05, 0.0501, 0.0505, 0.0509, 0.051, 0.052, 0.0525, 0.053, 0.054, 0.055, 0.056, 0.057, 0.0575, 0.058, 0.059, 0.0591, 0.0595, 0.0599, 0.06, 0.061, 0.065, 0.069, 0.07, 0.08, 0.09, 0.095, 0.099, 0.1, 0.101, 0.105, 0.11, 0.12, 0.13, 0.14, 0.15, 0.16, 0.17, 0.18, 0.19, 0.195, 0.199, 0.2, 0.201, 0.205, 0.21, 0.22, 0.225, 0.23, 0.24, 0.241, 0.245, 0.249, 0.25, 0.251, 0.255, 0.26, 0.27, 0.275, 0.28, 0.29, 0.291, 0.295, 0.299, 0.3, 0.31, 0.32, 0.325, 0.33, 0.34, 0.35, 0.36, 0.37, 0.375, 0.38, 0.39, 0.4, 0.41, 0.45, 0.49, 0.5, 0.51, 0.55, 0.59, 0.6, 0.7, 0.75, 0.8, 0.9, 0.91, 0.95, 0.99, 1, 1.01, 1.1, 1.2, 1.25, 1.3, 1.4, 1.5, 1.6, 1.7, 1.75, 1.8, 1.9, 1.95, 1.99, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 3.95, 3.99, 4, 4.01, 4.05, 4.09, 4.1, 4.15, 4.19, 4.2, 42.25, 4.3, 4.4, 4.5, 4.6, 4.7, 4.75, 4.8, 4.9, 4.95, 4.99, 5, 5.01, 5.05, 5.09, 5.1, 5.2, 5.25, 5.3, 5.4, 5.5, 5.6, 5.7, 5.75, 5.8, 5.9, 5.91, 5.95, 5.99, 6, 6.1, 6.5, 7, or 8 percent by weight. The rodenticide composition can include the hypercalcemia promoter in a percentage by weight of about a lower limit to about an upper limit, wherein the lower limit is a percentage by weight selected from the foregoing percentages by weight and the upper limit is a percentage by weight selected from the foregoing percentages by weight that is higher than the lower limit. In a preferred range, the rodenticide composition can include the hypercalcemia promoter in a percentage by weight of about 0.05% to about 4%. In a most preferred range, the rodenticide composition can include the hypercalcemia promoter in a percentage by weight of about 0.1% to about 3%. In an exemplary embodiment, the hypercalcemia promoter can be included in the composition at about 1% of the composition by weight.

The source of cellulose is a composition or ingredient that further increases dehydration once consumed by the rodent as part of the composition. The source of cellulose is selected from among: carboxymethyl cellulose, cardboard, cellulose acetate, regenerated cellulose, hydroxyethyl cellulose, hydroxypropyl cellulose, hydroxypropylmethyl cellulose, methylcellulose, pectin, sodium carboxymethyl cellulose, cornmeal, corn grits, corn cobs, corn gluten meal, any other suitable source of cellulose, a combination of two or more of the foregoing, or any other suitable material derived from any of the foregoing. The corn cobs can be ground corn cobs. In certain exemplary embodiments, the source of cellulose can be one or more naturally occurring compositions or ingredients. In other embodiments, the source of cellulose can be one or more artificial or manmade compositions or ingredients. In still other embodiments, the source of cellulose can be a mixture of one or more naturally occurring compositions or ingredients and one or more artificial or manmade compositions or ingredients. When utilizing naturally occurring cellulosic materials, the source of cellulose can be presoaked to remove phytic acid present in the natural source of cellulose. Phytic acid is known to bind to dietary calcium, which could inhibit the composition from causing hypercalcemia after ingestion by the rodent.

In preferred embodiments of the rodenticide composition, the source of cellulose is selected from among corn cobs, carboxymethyl cellulose, or a combination of the foregoing. In the most preferred embodiments of the rodenticide composition, the source of cellulose is corn cobs.

The source of cellulose may be included in the rodenticide composition in a percentage by weight of about 20% to about 60%. For example, the source of cellulose may be incorporated into the rodenticide composition in about 15, 16, 17, 17.5, 18, 18.5, 18.75, 18.9, 18.99, 19, 19.01, 19.05, 19.1, 19.2, 19.25, 19.3, 19.4, 19.41, 19.45, 19.49, 19.5, 19.51, 19.55, 19.59, 19.6, 19.7, 19.75, 19.8, 19.9, 19.91, 19.95, 19.99, 20, 20.01, 20.1, 20.2, 20.25, 20.3, 20.4, 20.5, 20.6, 20.7, 20.75, 20.8, 20.9, 20.95, 20.99, 21, 22, 23, 24, 25, 26, 27, 28, 29, 30, 35, 36, 37, 37.5, 38, 38.9, 39, 39.1, 39.2, 39.25, 39.3, 39.4, 39.5, 39.6, 39.7, 39.75, 39.8, 39, 39.1, 39.2, 39.25, 39.3, 39.4, 39.45, 39.5, 39.51, 39.55, 39.6, 39.7, 39.75, 39.8, 39.9, 39.95, 39.99, 40, 40.01, 40.05, 40.09, 40.1, 40.2, 40.25, 40.3, 40.4, 40.5, 40.6, 40.7, 40.75, 40.8, 40.9, 41, 42, 43, 44, 45, 46, 47, 48, 49, 50, 51, 52, 53, 54, 55, 56, 57, 58, 59, 59.1, 59.2, 59.25, 59.3, 59.4, 59.5, 59.6, 59.7, 59.75, 59.8, 59.9, 59.91, 59.95, 59.99, 60, 60.01, 60.05, 60.09, 60.1, 60.2, 60.25, 60.3, 60.4, 60.41, 60.45, 60.5, 60.51, 60.55, 60.59, 60.6, 60.7, 60.75, 60.8, 60.9, 60.91, 60.95, 60.99, 61, 61.01, 61.1, 61.25, 61.5, 62, 63, 64, or 65 percent by weight. The rodenticide composition can include the source of cellulose in a percentage by weight of about a lower limit to about an upper limit, wherein the lower limit is a percentage by weight selected from the foregoing percentages by weight and the upper limit is a percentage by weight selected from the foregoing percentages by weight that is higher than the lower limit. In a preferred range, the rodenticide composition can include the source of cellulose in a percentage by weight of about 20% to about 60%. In a most preferred range, the rodenticide composition can include the source of cellulose in a percentage by weight of about 30% to about 50%. In an exemplary embodiment, the source of cellulose can be included in the composition at about 40% of the composition by weight.

In some embodiments, the rodenticide can also include a composition or an ingredient that is an irritant for causing additional digestive stress. The irritant is selected from among: fish oil, caffeine, coffee grounds, sodium nitrite, citric acid, soybean oil, a magnesium-containing compound, any other suitable irritant, a combination of two or more of the foregoing, or any other suitable material derived from any of the foregoing. In certain exemplary embodiments, the irritant can be one or more naturally occurring compositions or ingredients. In other embodiments, the irritant can be one or more artificial or manmade compositions or ingredients. In still other embodiments, the irritant can be a mixture of one or more naturally occurring compositions or ingredients and one or more artificial or manmade compositions or ingredients. Some embodiments of the rodenticide composition may not include an irritant.

The magnesium-containing compound included in the rodenticide composition as an irritant is selected from among: magnesium sulfate, magnesium chloride, magnesium carbonate, magnesium bicarbonate, magnesium phosphate, magnesium hydroxide, magnesium oxide, any other suitable magnesium-containing compound, vinegar, ammonium benzoate, a combination of two or more of the foregoing, or any other suitable material derived from any of the foregoing.

In preferred embodiments of the rodenticide composition, the irritant is selected from among citric acid, coffee grounds, or both. In the most preferred embodiments of the rodenticide composition, the irritant is citric acid.

The irritant may be included in the rodenticide composition in a percentage by weight of about 0.25% to about 5%. For example, the irritant may be incorporated into the rodenticide composition in about 0.001, 0.005, 0.009, 0.01, 0.015, 0.019, 0.02, 0.025, 0.03, 0.04, 0.05, 0.06, 0.07, 0.08, 0.09, 0.095, 0.099, 0.1, 0.101, 0.105, 0.11, 0.12, 0.13, 0.14, 0.15, 0.16, 0.17, 0.18, 0.19, 0.195, 0.199, 0.2, 0.201, 0.205, 0.21, 0.22, 0.225, 0.23, 0.24, 0.241, 0.245, 0.249, 0.25, 0.251, 0.255, 0.26, 0.27, 0.275, 0.28, 0.29, 0.291, 0.295, 0.299, 0.3, 0.31, 0.32, 0.325, 0.33, 0.34, 0.35, 0.36, 0.37, 0.375, 0.38, 0.39, 0.4, 0.41, 0.45, 0.49, 0.5, 0.51, 0.55, 0.59, 0.6, 0.7, 0.75, 0.8, 0.9, 0.91, 0.95, 0.99, 1, 1.01, 1.1, 1.2, 1.25, 1.3, 1.4, 1.5, 1.6, 1.7, 1.75, 1.8, 1.9, 1.95, 1.99, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 3.95, 3.99, 4, 4.01, 4.05, 4.09, 4.1, 4.15, 4.19, 4.2, 4.225, 4.3, 4.4, 4.5, 4.6, 4.7, 4.75, 4.8, 4.9, 4.95, 4.99, 5, 5.01, 5.05, 5.09, 5.1, 5.2, 5.25, 5.3, 5.4, 5.5, 5.6, 5.7, 5.75, 5.8, 5.9, 5.91, 5.95, 5.99, 6, 6.1, 6.5, 7, 8, 9, or 10 percent by weight. The rodenticide composition can include the irritant in a percentage by weight of about a lower limit to about an upper limit, wherein the lower limit is a percentage by weight selected from the foregoing percentages by weight and the upper limit is a percentage by weight selected from the foregoing percentages by weight that is higher than the lower limit. In a preferred range, the rodenticide composition can include the irritant in a percentage by weight of about 0.25% to about 5%. In a most preferred range, the rodenticide composition can include the irritant in a percentage by weight of about 0.5% to about 3%. In an exemplary embodiment, the irritant can be included in the composition at about 1% of the composition by weight.

In some embodiments, the rodenticide can also include a composition or an ingredient that is a non-water soluble material that is a weathering agent for inhibiting deterioration in wet and damp environments. The non-water soluble material imparts weather resistance characteristics to the rodenticide composition so that the rodenticide to slow degradation of the rodenticide when it is exposed to the elements such as water (e.g., rain, dew, or other moisture). The non-water soluble material is selected from among: beeswax, paraffin wax, soybean oil, an ester of ammonia, an ester of butyl, an ester of calcium, an ester of glyceryl, fish oil, ammonium stearate, animal glue, any other suitable non-water soluble composition, a combination of two or more of the foregoing, or any other suitable material derived from any of the foregoing. In certain exemplary embodiments, the non-water soluble material can be one or more naturally occurring compositions or ingredients. In other embodiments, the non-water soluble material can be one or more artificial or manmade compositions or ingredients. In still other embodiments, the non-water soluble material can be a mixture of one or more naturally occurring compositions or ingredients and one or more artificial or manmade compositions or ingredients. The non-water soluble material can be included as an ingredient of the rodenticide, or the non-water soluble material can be applied to the rodenticide, e.g., by pouring or spraying it onto the rodenticide. Some embodiments of the rodenticide composition may not include a non-water soluble material.

In preferred embodiments of the rodenticide composition, the non-water soluble material is selected from among beeswax, paraffin wax, or both. In the most preferred embodiments of the rodenticide composition, the non-water soluble material is paraffin wax.

The non-water soluble material may be included in the rodenticide composition in a percentage by weight of about 2% to about 10%. For example, the non-water soluble material may be incorporated into the rodenticide composition in about 0.1, 0.101, 0.105, 0.11, 0.12, 0.13, 0.14, 0.15, 0.16, 0.17, 0.18, 0.19, 0.195, 0.199, 0.2, 0.201, 0.205, 0.21, 0.22, 0.225, 0.23, 0.24, 0.241, 0.245, 0.249, 0.25, 0.251, 0.255, 0.26, 0.27, 0.275, 0.28, 0.29, 0.291, 0.295, 0.299, 0.3, 0.31, 0.32, 0.325, 0.33, 0.34, 0.35, 0.36, 0.37, 0.375, 0.38, 0.39, 0.4, 0.41, 0.45, 0.49, 0.5, 0.51, 0.55, 0.59, 0.6, 0.7, 0.75, 0.8, 0.9, 0.91, 0.95, 0.99, 1, 1.01, 1.1, 1.2, 1.25, 1.3, 1.4, 1.5, 1.6, 1.7, 1.75, 1.8, 1.9, 1.95, 1.99, 2, 2.1, 2.2, 2.25, 2.3, 2.4, 2.5, 2.6, 2.7, 2.75, 2.8, 2.9, 2.91, 2.95, 2.99, 3, 3.1, 3.15, 3.19, 3.2, 3.25, 3.3, 3.4, 3.5, 3.6, 3.7, 3.75, 3.8, 3.9, 3.95, 3.99, 4, 4.01, 4.05, 4.09, 4.1, 4.15, 4.19, 4.2, 42.25, 4.3, 4.4, 4.5, 4.6, 4.7, 4.75, 4.8, 4.9, 4.95, 4.99, 5, 5.01, 5.05, 5.09, 5.1, 5.2, 5.25, 5.3, 5.4, 5.5, 5.6, 5.7, 5.75, 5.8, 5.9, 5.91, 5.95, 5.99, 6, 6.1, 6.2, 6.25, 6.3, 6.4, 6.5, 6.6, 6.7, 6.75, 6.8, 6.9, 6.91, 6.95, 6.99, 7, 7.01, 7.09, 7.1, 7.15, 7.2, 7.25, 7.3, 7.4, 7.5, 7.6, 7.7, 7.75, 7.8, 7.9, 7.95, 7.99, 8, 8.1, 8.2, 8.25, 8.3, 8.4, 8.5, 8.6, 8.7, 8.75, 8.8, 8.9, 9, 9.1, 9.2, 9.25, 9.3, 9.4, 9.5, 9.6, 9.7, 9.75, 9.8, 9.9, 9.91, 9.95, 9.99, 10, 10.1, 10.2, 10.25, 10.3, 10.4, 10.5, 10.6, 10.7, 10.75, 10.8, 10.9, 11, 12, 13, 14, or 15 percent by weight. The rodenticide composition can include the non-water soluble material in a percentage by weight of about a lower limit to about an upper limit, wherein the lower limit is a percentage by weight selected from the foregoing percentages by weight and the upper limit is a percentage by weight selected from the foregoing percentages by weight that is higher than the lower limit. In a preferred range, the rodenticide composition can include the non-water soluble material in a percentage by weight of about 2% to about 10%. In a most preferred range, the rodenticide composition can include the non-water soluble material in a percentage by weight of about 3% to about 7%. In an exemplary embodiment, the non-water soluble material can be included in the composition at about 5% of the composition by weight.

In some embodiments, the rodenticide can also include a composition or an ingredient that is a flavoring to serve as an attractant to rodents. The flavoring is selected from among: cocoa, peanut butter, cheese, egg yolk, sulfur, fish oil, fish meal, dimethyl disulfide, syrup, peanuts, sorbitol, sucralose, sucrose, fructose, molasses, cat food, malt flavor, nutria meat, dried blood, any other suitable flavoring, a combination of two or more of the foregoing, or any other suitable material derived from any of the foregoing. In other embodiments, the flavoring can be one or more artificial or manmade compositions or ingredients. In still other embodiments, the flavoring can be a mixture of one or more naturally occurring compositions or ingredients and one or more artificial or manmade compositions or ingredients. Some embodiments of the rodenticide composition may not include a flavoring.

In preferred embodiments of the rodenticide composition, the flavoring is selected from among sorbitol, fructose, natural cheese, egg yolk, or a combination of two or more of the foregoing. In the most preferred embodiments of the rodenticide composition, the flavoring is selected from among natural cheese, egg yolk, or both because they also aid in the promotion of hypercalcemia due to their naturally occurring cholecalciferol content.

The flavoring may be included in the rodenticide composition in a percentage by weight of about 0.5% to about 6%. For example, the flavoring may be incorporated into the rodenticide composition in about 0.001, 0.005, 0.009, 0.01, 0.015, 0.019, 0.02, 0.025, 0.03, 0.035, 0.039, 0.04, 0.041, 0.042, 0.0425, 0.043, 0.044, 0.045, 0.046, 0.047, 0.0475, 0.048, 0.049, 0.0491, 0.0495, 0.0499, 0.05, 0.0501, 0.0505, 0.0509, 0.051, 0.052, 0.0525, 0.053, 0.054, 0.055, 0.056, 0.057, 0.0575, 0.058, 0.059, 0.0591, 0.0595, 0.0599, 0.06, 0.061, 0.065, 0.069, 0.07, 0.08, 0.09, 0.095, 0.099, 0.1, 0.101, 0.105, 0.11, 0.12, 0.13, 0.14, 0.15, 0.16, 0.17, 0.18, 0.19, 0.195, 0.199, 0.2, 0.201, 0.205, 0.21, 0.22, 0.225, 0.23, 0.24, 0.241, 0.245, 0.249, 0.25, 0.251, 0.255, 0.26, 0.27, 0.275, 0.28, 0.29, 0.291, 0.295, 0.299, 0.3, 0.31, 0.32, 0.325, 0.33, 0.34, 0.35, 0.36, 0.37, 0.375, 0.38, 0.39, 0.4, 0.41, 0.45, 0.49, 0.5, 0.51, 0.55, 0.59, 0.6, 0.7, 0.75, 0.8, 0.9, 0.91, 0.95, 0.99, 1, 1.01, 1.1, 1.2, 1.25, 1.3, 1.4, 1.5, 1.6, 1.7, 1.75, 1.8, 1.9, 1.95, 1.99, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 3.95, 3.99, 4, 4.01, 4.05, 4.09, 4.1, 4.15, 4.19, 4.2, 42.25, 4.3, 4.4, 4.5, 4.6, 4.7, 4.75, 4.8, 4.9, 4.95, 4.99, 5, 5.01, 5.05, 5.09, 5.1, 5.2, 5.25, 5.3, 5.4, 5.5, 5.6, 5.7, 5.75, 5.8, 5.9, 5.91, 5.95, 5.99, 6, 6.1, 6.2, 6.25, 6.3, 6.4, 6.5, 6.6, 6.7, 6.75, 6.8, 6.9, 6.91, 6.95, 6.99, 7, 7.01, 7.09, 7.1, 7.15, 7.2, 7.25, 7.3, 7.4, 7.5, 7.6, 7.7, 7.75, 7.8, 7.9, 7.95, 7.99, 8, 8.1, 8.2, 8.25, 8.3, 8.4, 8.5, 8.6, 8.7, 8.75, 8.8, 8.9, 9, 9.1, 9.2, 9.25, 9.3, 9.4, 9.5, 9.6, 9.7, 9.75, 9.8, 9.9, 9.91, 9.95, 9.99, 10, 10.1, 10.2, 10.25, 10.3, 10.4, 10.5, 10.6, 10.7, 10.75, 10.8, 10.9, 11, 12, 13, 14, or 15 percent by weight. The rodenticide composition can include the flavoring in a percentage by weight of about a lower limit to about an upper limit, wherein the lower limit is a percentage by weight selected from the foregoing percentages by weight and the upper limit is a percentage by weight selected from the foregoing percentages by weight that is higher than the lower limit. In a preferred range, the rodenticide composition can include the flavoring in a percentage by weight of about 0.5% to about 6%. In a most preferred range, the rodenticide composition can include the flavoring in a percentage by weight of about 1% to about 4%. In an exemplary embodiment, the flavoring can be included in the composition at about 2% of the composition by weight.

In some exemplary embodiments, the rodenticide composition further includes one or more coloring agents. The coloring agent of the rodenticide is selected from among: FD&C Red No. 3, FD&C Red No. 40, red cabbage color, FD&C Yellow No. 5, FD&C Yellow No. 6, FD&C Blue No.

1, C.I. Pigment Blue No. 29, FD&C Blue No. 2, FD&C Green No. 3, any other suitable coloring agent, a combination of two or more of the foregoing, or any other suitable material derived from any of the foregoing. In other embodiments, the coloring agent can be one or more artificial or manmade compositions or ingredients. In still other embodiments, the coloring agent can be a mixture of one or more naturally occurring compositions or ingredients and one or more artificial or manmade compositions or ingredients. Some embodiments of the rodenticide composition may not include a coloring agent.

In preferred embodiments of the rodenticide composition, the coloring agent is selected from among any red coloring agent above or a combination of two or more red coloring agents, any yellow color agent above or a combination of two or more yellow coloring agents, or a combination of two or more of the foregoing. Rodents, and rats and mice in particular, are attracted to the color red, and to a lesser degree, to the color yellow. In the most preferred embodiments of the rodenticide composition, the coloring agent is red cabbage color.

In one embodiment, the rodenticide includes: a dehydrant that includes cellulose fibers, silica gel, perlite, sodium chloride, or combinations thereof; a composition for producing endogenous gas, wherein the gas is oxygen and the composition for producing endogenous gas is selected from among calcium percarbonate, calcium peroxide, or combinations thereof; a dietary emulsifier that includes carboxymethyl cellulose, polyoxyethylene (20) sorbitan monooleate, or both; a hypercalcemia promoter that includes a mixture of calcium carbonate and cholecalciferol; an irritant; and a source of cellulose. In exemplary embodiments of this composition, the dehydrant includes cellulose fibers, silica gel, or both. In exemplary embodiments of this composition, the composition for producing endogenous gas is calcium percarbonate. In exemplary embodiments of this composition, the dietary emulsifier is polyoxyethylene (20) sorbitan monooleate. In exemplary embodiments of this composition, the hypercalcemia promoter includes a mixture of calcium carbonate, cholecalciferol, and L-lysine. In exemplary embodiments of this composition, the source of cellulose includes corn cobs, carboxymethyl cellulose, or both. In some embodiments of this composition, the rodenticide may further include an irritant. The irritant can be citric acid, coffee grounds, or both. In some embodiments of this composition, the rodenticide may also include a non-water soluble material that inhibits deterioration in wet and damp environments.

In another embodiment, the rodenticide includes a mixture of: a dehydrant that includes cellulose fibers, silica gel, or combinations thereof; a composition for producing endogenous gas, wherein the gas is oxygen and the composition for producing endogenous gas is calcium percarbonate; a dietary emulsifier that is polyoxyethylene (20) sorbitan monooleate; a hypercalcemia promoter that includes a mixture of calcium carbonate, cholecalciferol, and L-lysine; an irritant that includes fish oil, caffeine, coffee grounds, sodium nitrite, citric acid, soybean oil, a magnesium-containing compound, combinations thereof, or any other suitable material derived from any of the foregoing; and a source of cellulose. In exemplary embodiments of this composition, the irritant includes citric acid, coffee grounds, or both. In exemplary embodiments of this composition, the source of cellulose includes corn cobs, carboxymethyl cellulose, or both. In exemplary embodiments of this composition, the rodenticide composition further includes a non-water soluble material that inhibits deterioration in wet and damp environments.

The rodenticide composition can be produced as cakes, caplets, cookies, pellets, powders, tablets, or any other suitable form for consumption by rodents for which extermination is desired.

Example 1

One exemplary embodiment of the rodenticide composition includes perlite at 43% by weight, calcium peroxide at 6% by weight, cellulose at 46% by weight, magnesium carbonate at 1% by weight, cholecalciferol at 0.5% by weight, L-lysine at 1.5% by weight, and cheese flavoring at 2% by weight.

Example 2

Another exemplary embodiment of the rodenticide composition includes alpha cellulose at 86% by weight, sodium perborate at 5% by weight, carboxymethyl cellulose at 1% by weight, coffee grounds at 3% by weight, calcium citrate at 1.2% by weight, ergocalciferol at 0.8% by weight, and peanut butter flavoring at 3% by weight.

Example 3

Another exemplary embodiment of the rodenticide composition includes silica gel at 27.5% by weight, magnesium percarbonate at 4% by weight, polysorbate-80 at 2% by weight, caffeine at 0.5% by weight, calcium citrate at 2% by weight, L-Lysine at 1% by weight, cellulose at 60% by weight, and cocoa at 3% by weight.

The invention also features a method for exterminating rodents. The method includes the steps of preparing a rodenticide composition such as the ones described herein and placing an amount of the rodenticide composition sufficient to kill a rodent in an area in which the extermination of rodents is desired, wherein the rodent is killed after consuming the rodenticide composition. The rodenticide composition used in this method may include or have applied to it (by pouring, spraying, or other means) an irritant, a non-water soluble material that inhibits deterioration in wet and damp environments or both.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A rodenticide comprising a mixture of:
a dehydrant;
a composition for producing endogenous gas;
a dietary emulsifier comprising one or more dietary emulsifiers selected from the group consisting of: carboxymethylcellulose and polyoxyethylene (20) sorbitan monooleate;
a hypercalcemia promoter;
a composition for further increasing dehydration of a rodent; and a non-water soluble material that inhibits deterioration in wet and damp environments.

2. The rodenticide of claim 1, wherein the dehydrant comprises one or more dehydrants selected from the group consisting of: a grain-based cellulosic composition, a nut-based cellulosic composition, a legume-based cellulosic composition, a starchy tuber-based cellulosic composition, cellulose fibers, activated alumina, aerogel, benzophenone, bentonite clay, calcium chloride, calcium sulfate, caramel, cobalt (II) chloride, copper (II) sulfate, ethanol, glycerol, honey, lithium bromide, lithium chloride, magnesium perchlorate, magnesium sulfate, methanol, perlite, potassium carbonate, potassium hydroxide, silica, silica gel, fumed silica, sodium, sodium chlorate, sodium chloride, sodium hydroxide, sucrose, sulfuric acid, vermiculite, and zinc chloride.

3. The rodenticide of claim 1, wherein the composition for producing endogenous gas comprises one or more compositions selected from the group consisting of: an alkali carbonate, a peroxide, and yeast.

4. The rodenticide of claim 1, wherein the composition for producing endogenous gas comprises one or more compositions selected from the group consisting of: sodium percarbonate, magnesium percarbonate, zinc percarbonate, calcium peroxide, calcium percarbonate, magnesium peroxide, zinc peroxide, sodium perborate, potassium monopersulfate, tetraacetylethylenediamine, and yeast.

5. The rodenticide of claim 1, wherein the hypercalcemia promoter comprises one or more hypercalcemia promoters selected from the group consisting of: calcium carbonate, calcium glycerate, calcium citrate, calcium lactate, calcium gluconate, a calcium uptake enhancer, and bone meal.

6. The rodenticide of claim 5, wherein the calcium uptake enhancer comprises one or more calcium uptake enhancers selected from the group consisting of: cholecalciferol, ergocalciferol, L-lysine, L-Valine, and L-tryptophan.

7. The rodenticide of claim 1, wherein the source of cellulose composition for further increasing dehydration of a rodent comprises one or more compositions selected from the group consisting of: carboxymethyl cellulose, cardboard, cellulose acetate, regenerated cellulose, hydroxyethyl cellulose, hydroxypropyl cellulose, hydroxypropylmethyl cellulose, methylcellulose, pectin, sodium carboxymethyl cellulose, cornmeal, corn grits, corn cobs, and corn gluten meal.

8. The rodenticide of claim 1, further comprising an irritant, wherein the irritant comprises one or more irritants selected from the group consisting of: fish oil, caffeine, coffee grounds, sodium nitrite, citric acid, soybean oil, a magnesium-containing compound, vinegar, and ammonium benzoate.

9. The rodenticide of claim 8, wherein the magnesium-containing compound comprises one or more compounds selected from the group consisting of: magnesium sulfate, magnesium chloride, magnesium carbonate, magnesium bicarbonate, magnesium phosphate, magnesium hydroxide, and magnesium oxide.

10. The rodenticide of claim 1, wherein the non-water soluble material comprises one or more materials selected from the group consisting of: beeswax, paraffin wax, soybean oil, an ester of ammonia, an ester of butyl, an ester of calcium, an ester of glyceryl, fish oil, ammonium stearate, and animal glue.

11. The rodenticide of claim 1, further comprising a flavoring, wherein the flavoring comprises one or more flavorings selected from the group consisting of: cocoa, peanut butter, cheese, egg yolk, sulfur, fish oil, fish meal, dimethyl disulfide, syrup, peanuts, sorbitol, sucralose, sucrose, fructose, molasses, cat food, malt flavor, nutria meat, and dried blood.

12. The rodenticide of claim 1, further comprising a coloring agent, wherein the coloring agent comprises one or more coloring agents selected from the group consisting of: FD&C Red No. 3, FD&C Red No. 40, red cabbage color, FD&C Yellow No. 5, FD&C Yellow No. 6, FD&C Blue No. 1, C.I. Pigment Blue No. 29, FD&C Blue No. 2, and FD&C Green No. 3.

13. A rodenticide comprising a mixture of:
a dehydrant comprising one or more dehydrants selected from the group consisting of: cellulose fibers, silica gel, perlite, and sodium chloride;
a composition for producing endogenous gas, wherein the gas comprises oxygen and the composition for producing endogenous gas comprises one or more compositions selected from the group consisting of: calcium percarbonate and calcium peroxide;
a dietary emulsifier comprising one or more dietary emulsifiers selected from the group consisting of: carboxymethylcellulose and polyoxyethylene (20) sorbitan monooleate;
a hypercalcemia promoter comprising a mixture of calcium carbonate and cholecalciferol;
an irritant;
a source of cellulose; and
a non-water soluble material that inhibits deterioration in wet and damp environments.

14. The rodenticide of claim 13, wherein the dehydrant comprises one or more dehydrants selected from the group consisting of: cellulose fibers and silica gel.

15. The rodenticide of claim 13, wherein the composition for producing endogenous gas comprises calcium percarbonate.

16. The rodenticide of claim 13, wherein the dietary emulsifier comprises polyoxyethylene (20) sorbitan monooleate.

17. The rodenticide of claim 13, wherein the hypercalcemia promoter comprises a mixture of calcium carbonate, cholecalciferol, and L-lysine.

18. The rodenticide of claim 13, wherein the source of cellulose comprises one or more sources selected from the group consisting of: corn cobs and carboxymethyl cellulose.

19. The rodenticide of claim 13, further comprising an irritant, wherein the irritant comprises one or more irritants selected from the group consisting of: citric acid and coffee grounds.

20. The rodenticide of claim 13, further comprising a coloring agent selected from the group consisting of: a red coloring agent and a yellow coloring agent.

21. A rodenticide comprising a mixture of:
a dehydrant comprising one or more dehydrants selected from the group consisting of: cellulose fibers and silica gel;
a composition for producing endogenous gas, wherein the gas comprises oxygen and the composition for producing endogenous gas comprises calcium percarbonate;
a dietary emulsifier comprising polyoxyethylene (20) sorbitan monooleate;
a hypercalcemia promoter comprising a mixture of calcium carbonate, cholecalciferol, and L-lysine;
an irritant comprising one or more irritants selected from the group consisting of: fish oil, caffeine, coffee grounds, sodium nitrite, citric acid, soybean oil, and a magnesium-containing compound;
a source of cellulose; and a non-water soluble material that inhibits deterioration in wet and damp environments.

22. The rodenticide of claim 21, wherein the irritant comprises one or more irritants selected from the group consisting of: citric acid and coffee grounds.

23. The rodenticide of claim 21, wherein the source of cellulose comprises one or more sources selected from the group consisting of: corn cobs and carboxymethyl cellulose.

24. The rodenticide of claim 21, further comprising a coloring agent selected from the group consisting of: a red coloring agent and a yellow coloring agent.

25. A rodenticide comprising a mixture of:
    a dehydrant comprising one or more dehydrants selected from the group consisting of: cellulose fibers, silica gel, and perlite;
    a composition for producing endogenous gas, the composition comprising one or more compositions selected from the group consisting of: calcium percarbonate, sodium percarbonate, and calcium peroxide;
    a dietary emulsifier comprising one or more dietary emulsifiers selected from the group consisting of: carboxymethylcellulose and polyoxyethylene (2) sorbitan monooleate;
    a hypercalcemia promoter comprising one or more hypercalcemia promoters selected from the group consisting of: calcium carbonate, calcium citrate, and calcium lactate;
    a source of cellulose comprising one or more sources selected from the group consisting of: corn cobs, corn gluten meal, and regenerated cellulose;
    an irritant comprising one or more irritants selected from the group consisting of: fish oil, citric acid, and coffee grounds;
    a non-water soluble material that inhibits deterioration in wet and damp environments, the non-water soluble material comprising one or more materials selected from the group consisting of: paraffin wax, beeswax, and soybean oil; and
    a flavoring.

26. A method for exterminating rodents comprising the steps of:
    (a) preparing a rodenticide composition comprising a mixture of:
        a dehydrant comprising one or more dehydrants selected from the group consisting of: cellulose fibers, silica gel, perlite, and sodium chloride;
        a composition for producing endogenous gas, wherein the gas comprises oxygen and the composition for producing endogenous gas comprises one or more compositions selected from the group consisting of: calcium percarbonate and calcium peroxide;
        a dietary emulsifier comprising one or more dietary emulsifiers selected from the group consisting of: carboxymethylcellulose and polyoxyethylene (20) sorbitan monooleate;
        a hypercalcemia promoter comprising a mixture of calcium carbonate and cholecalciferol;
        an irritant;
        a source of cellulose; and
        a non-water soluble material that inhibits deterioration in wet and damp environments; and
    (b) placing an amount of the rodenticide composition sufficient to kill a rodent in an area in which the extermination of rodents is desired, wherein the rodent is killed after consuming the rodenticide composition.

27. The method of claim 26, wherein the rodenticide composition further comprises
    a coloring agent.

* * * * *